(12) United States Patent
Poynard (10) Patent No.: US 10,198,552 B2
(45) Date of Patent: Feb. 5, 2019

(54) METHOD OF DIAGNOSIS OF FIBROTIC DISEASES

(71) Applicants: Assistance Publique-Hôpitaux de Paris, Paris (FR); Biopredictive, Paris (FR)

(72) Inventor: Thierry Poynard, Paris (FR)

(73) Assignees: ASSISTANCE PUBLIQUE—HOPITAUX DE PARIS, Paris (FR); BIOPREDICTIVE, Paris (FR)

(*) Notice: Subject to any disclaimer, the term of this patent is extended or adjusted under 35 U.S.C. 154(b) by 687 days.

(21) Appl. No.: 14/361,998

(22) PCT Filed: Nov. 30, 2012

(86) PCT No.: PCT/EP2012/074177
§ 371 (c)(1),
(2) Date: May 30, 2014

(87) PCT Pub. No.: WO2013/079711
PCT Pub. Date: Jun. 6, 2013

(65) Prior Publication Data
US 2014/0329260 A1  Nov. 6, 2014

(30) Foreign Application Priority Data

Dec. 2, 2011 (EP) ..................................... 11306611

(51) Int. Cl.
| | | |
|---|---|---|
| C12Q 1/48 | (2006.01) | |
| G01N 33/50 | (2006.01) | |
| G06F 19/00 | (2018.01) | |
| G06F 19/18 | (2011.01) | |
| G16H 50/20 | (2018.01) | |

(52) U.S. Cl.
CPC ............... G06F 19/18 (2013.01); C12Q 1/48 (2013.01); G01N 33/5091 (2013.01); G06F 19/00 (2013.01); G16H 50/20 (2018.01)

(58) Field of Classification Search
None
See application file for complete search history.

(56) References Cited

U.S. PATENT DOCUMENTS

| | | |
|---|---|---|
| 6,986,995 B2 | 1/2006 | Rose et al. |
| 7,225,080 B2 | 5/2007 | Poynard |
| 7,856,319 B2 | 12/2010 | Poynard |
| 7,860,656 B2 | 12/2010 | Poynard |
| 8,489,335 B2 | 7/2013 | Cales |
| 2003/0175686 A1 | 9/2003 | Rose et al. |
| 2004/0039553 A1 | 2/2004 | Poynard |
| 2006/0084057 A1 | 4/2006 | Rose et al. |
| 2006/0172286 A1 | 8/2006 | Poynard |
| 2006/0173629 A1 | 8/2006 | Poynard |
| 2008/0145864 A1 | 6/2008 | Poynard |
| 2009/0111132 A1 | 4/2009 | Poynard |
| 2009/0143993 A1 | 6/2009 | Cales |
| 2011/0306849 A1 | 12/2011 | Cales et al. |
| 2011/0313276 A1 | 12/2011 | Cales et al. |
| 2013/0029863 A1 | 1/2013 | Ruppe et al. |

FOREIGN PATENT DOCUMENTS

| | | |
|---|---|---|
| WO | WO-2002/016949 A1 | 2/2002 |
| WO | WO-2005/116901 A2 | 12/2005 |
| WO | WO-2006/082522 A1 | 8/2006 |
| WO | WO-2006/103570 A2 | 10/2006 |
| WO | WO-2010/058295 A2 | 5/2010 |
| WO | WO-2010/097472 A1 | 9/2010 |
| WO | WO-2010/149767 A1 | 12/2010 |
| WO | WO-2011/039321 A1 | 4/2011 |
| WO | WO-2011/064324 A1 | 6/2011 |
| WO | WO-2003/073822 | 9/2013 |

OTHER PUBLICATIONS

Vergniol et al. Noninvasive Tests for Fibrosis and Liver Stiffness Predict 5-year Outcomes fo Patients With Chronic Hepatitis C Gastroenterology vol. 140, pp. 1970-1979 (2011).*
Henderson et al. Identification and efficacy of longitudinal markers for survival Biostatistics vol. 3, pp. 33-50 (Year: 2002).*
Castéra, L. et al., "Prospective Comparison of Transient Elastography, Fibrotest, APRI, and Liver Biopsy for the Assessment of Fibrosis in Chronic Hepatitis C." *Gastroenterology* 128: 343-350 (2005).
Shaheen, A.A.M. et al., "FibroTest and FibroScan for the Prediction of Hepatitis C-Related Fibrosis: A Systematic Review of Diagnostic Test Accuracy." *American Journal of Gastroenterology* 102: 2589-2600 (2007).
Bedossa, P. et al., "Sampling variability of liver fibrosis in chronic hepatitis C." *Hepatology* 38: 1449-57 (2003).
Bedossa, P. et al., "An algorithm for the grading of activity in chronic hepatitis C. The METAVIR Cooperative Study Group." *Hepatology* 24: 289-293 (1996).
Boursier, J et al., "A new combination of blood test and fibroscan for accurate non-invasive diagnosis of liver fibrosis stages in chronic hepatitis C." *Am J Gastroenterol.* 106:1255-63 (2011).
Bousier, J. et al., "Comparison of 8 diagnostic algorithms for liver fibrosis in hepatitis C: New algorithms are more precise and entirely non-invasive." *Hepatology* 55(1): 58-67 (2012).
Boursier, J. et al., "The combination of a blood test and Fibroscan improves the non-invasive diagnosis of liver fibrosis." *Liver Int.* 29:1507-15 (2009).
Castéra, L. et al., "Pitfalls of liver stiffness measurement: a 5-year prospective study of 13,369 examinations." *Hepatology* 51:828:35 (2010).
Castera, L. et al., "Non-invasive assessment of liver fibrosis: are we ready?" *Lancet* 375:1419-1420 (2010).
Friedrich-Rust, M. et al., "Performance of transient elastography for the staging of liver fibrosis: a meta-analysis." *Gastroenterology* 134: 960-974 (2008).

(Continued)

*Primary Examiner* — John S Brusca
(74) *Attorney, Agent, or Firm* — Polsinelli PC (57) ABSTRACT

The present invention relates to a new diagnosis method in the field of hepatology, combining measurement of serum markers and of liver elasticity.

5 Claims, 1 Drawing Sheet

(56) References Cited

OTHER PUBLICATIONS

Hadgu, A. et al., "A biomedical application of latent class models with random effects." *Applied Statistics* 47, 603-616 (1998).
Haute Autorité De Santé, "Méthodes non invasives d'évaluation de la fibrose/cirrhose hépatique." pp. 1-5 (Dec. 2006).
Hintze, J.L., "NCSS 2007 User's Guide I." Number Cruncher Statistical Systems Software NCSS, Kaysville, Utah (2007).
Hintze, J.L., "NCSS 2007 User's Guide II." Number Cruncher Statistical Systems Software NCSS, Kaysville, Utah (2007).
Hintze, J.L., "NCSS 2007 User's Guide III." Number Cruncher Statistical Systems Software NCSS, Kaysville, Utah (2007).
Hintze, J.L., "NCSS 2007 User's Guide IV." Number Cruncher Statistical Systems Software NCSS, Kaysville, Utah (2007).
Hintze, J.L., "NCSS 2007 User's Guide V." Number Cruncher Statistical Systems Software NCSS, Kaysville, Utah (2007).
Lambert, J. et al., "How to measure the diagnostic accuracy of noninvasive liver fibrosis indices: the area under the ROC curve revisited," *Clin Chem.* 54:1372-8 (2008).
Lucidarme, D. et al., "Factors of accuracy of transient elastography (FibroScan®) for the diagnosis of liver fibrosis in chronic hepatitis C." *Hepatology* 49(4):1083-9 (2009).
Mehta, S.H. et al., "Exceeding the limits of liver histology markers." *J Hepatol* 50:36-41 (2009).
Munteanu, M. et al., "The risk of multiplying diagnostic combinations in the absence of a perfect gold standard for a fibrosis test." *Am J Gastroenterol* 106:1853 (2011).
Myers, R.P. et al., "Prevalence, risk factors and causes of discordance in fibrosis staging by transient elastography and liver biopsy." *Liver Int* 30:1471-80 (2010).
Nguyen, D. et al., "Noninvasive assessment of liver fibrosis." *Hepatology* 53:2107-10 (2011).
Poynard, T., "First-line assessment of patients with chronic liver disease with non-invasive techniques and without recourse to liver biopsy." *J Hepatol* 54:586-7 (2011).
Poynard, T. et al., "Concordance in a world without a gold standard: a new non-invasive methodology for improving accuracy of fibrosis markers." PLoS ONE 3(12): e3857.doi:10.1371/journal.pone.0003857 (2008).
Poynard, T. et al., "Applicability and precautions of use of liver injury biomarker FibroTest. A reappraisal at 7 years of age." *BMC Gastroenterol* 11:39 (2011).
Poynard, T. et al., "Prognostic value of liver fibrosis biomarkers: a metaanalysis." *Gastroenterol Hepatol* 7:445-54 (2011).
Poynard, T. et al., "FibroTest and Fibroscan performances revisited in patients with chronic hepatitis C. Impact of the spectrum effect and the applicability rate." *Clin Res Hepatol Gastroenterol* 35:720-1 (Aug. 17, 2011).
Poynard, T. et al., "Relative performances of FibroTest, Fibroscan and biopsy for assessing the stage of liver fibrosis in patients with chronic hepatitis C: a step toward the truth in the absence of a gold standard." *J Hepatol* 56:541-548 (2012).
Qu, Y. et al., "Random effects models in latent class analysis for evaluating accuracy of diagnostic tests." *Biometrics* 52:797-810 (1996).
Rousselet, M.C. et al., "Hepatitis Network 49. Sources of variability in histological scoring of chronic viral hepatitis." *Hepatology* 41:257-64 (2005).
Rutjes, A.W. et al., "Evaluation of diagnostic tests when there is no gold standard. A review of methods." *Health Technol Assess* 11:1-51 (2007).
Sebastiani, C. et al., "SAFE biopsy: a validated method for large-scale staging of liver fibrosis in chronic hepatitis C." *Hepatology* 49:1821-7 (2009).
Vergniol, J. et al., "Non-invasive tests for fibrosis and liver stiffness predict 5-year outcomes of patients with chronic hepatitis C." *Gastroenterology* 140:1970-9 (2011).
Vermunt, J.K. et al., "Technical Guide for Latent GOLD 4.0: Basic and Advanced." Belmont Massachusetts: Statistical Innovations Inc (2005).

* cited by examiner

METHOD OF DIAGNOSIS OF FIBROTIC DISEASES

RELATED APPLICATIONS

This application is a national stage application (under 35 U.S.C. § 371) of PCT/EP2012/074177, filed Nov. 30, 2012, which claims priority of European Application 11306611.2, filed Dec. 2, 2011.

The present invention relates to a new diagnosis method in the field of hepatology, as well as to a generic method for improving the diagnosis tests in the absence of a gold standard.

In the last few years, different diagnosis methods have been developed to allow detection of liver disease through measurement of serum markers, in place of liver biopsy. One can cite in particular FibroTest® (FT) described in WO 2002/016949, marketed by Biopredictive (Paris, France), and liver stiffness measurement (LSM) using Fibroscan®, marketed by Echosens (Paris, France).

Use of these methods made it possible to reduce the number of biopsies, previously considered as mandatory for the management of patients with liver disease, (in particular in patients infected by the hepatitis C virus (HCV)), particularly for the staging of fibrosis. Liver biopsy is indeed an aggressive procedure.

FibroTest® (FT), and liver stiffness measurement (LSM) using Fibroscan® are now the most validated techniques for the non-invasive assessment of fibrosis stages in patients with chronic hepatitis C (CHC) [1-3]. Since the first study by Castera et al [4], several studies have assessed combinations between FT or other biomarkers with LSM [5-8]. None of these studies have used the most appropriate statistical methods, taking into account the applicability rate and the spectrum effect [9-11], and methods assuming that liver biopsy is not a perfect gold standard [9,12-13].

Indeed, even a biopsy specimen of 25 mm length has more than 20% of false positive or false negative for staging fibrosis versus large surgical biopsies [13-15]. Therefore classical estimates of accuracy (sensitivity, specificity and area under the ROC curves [AUROC]) of diagnostic test are false [12]. The magnitude of the impact of this error of biopsy is so important that the AUROC determinations>0.90 could not be achieved even for a marker that perfectly measured disease [16].

It is reminded that an ideal "gold standard" test has a sensitivity of 100% with respect to the presence of the disease (it identifies all individuals with a well defined disease process; it does not have any false-negative results) and a specificity of 100% (it does not falsely identify someone with a condition that does not have the condition; it does not have any false-positive results).

Some gold standard test with a sensitivity and specificity very close to 100% exist for some disease. As an illustration, detection of DNA or antibodies specific to a disease determinant would indicate that said disease is present. The sensitivity may still not be exactly 100%, as some patients may have the disease, with the DNA or antibodies not detectable (for example if the infection was recent).

The quality of a diagnosis test may be determined by drawing a Receiving Operating Characteristic (ROC) curve and measuring the Area Under Receiving Operating Characteristic curve (AUROC).

The ROC curve is drawn by plotting the sensitivity versus (1-specificity), after classification of the patients, according to the result obtained for the diagnosis test, for different thresholds (from 0 to 1).

For the gold standard test, the AUROC is 1 or very close to 1.

It is usually acknowledged that a ROC curve the area under which has a value superior to 0.7 is a good predictive curve for diagnosis. The ROC curve has to be acknowledged as a curve allowing prediction of the quality of a diagnosis test. It is best for the AUROC to be as closed as 1 as possible, this value describing a test which is 100% specific and sensitive.

Nevertheless, as indicated above, and since liver biopsy may not be considered to be a gold standard for liver fibrosis, it is not possible to go beyond 0.9 for non-invasive diagnosis methods for this disease.

It is thus necessary to continue to improve the non-invasive diagnosis methods, taking into account this lack of reliability of liver biopsy in some cases. Use a specific statistical methods are thus needed.

Using methods without using a Gold Standard ("truth without a gold standard" [TAGS]), the inventor observed that the isolated performance of FT and LSM were similar for the diagnosis of cirrhosis and in favor of FibroTest for the diagnosis of advanced fibrosis, with a higher sensitivity using the standard cut-off.

In the present invention, a new algorithm combining FT and LCM (ElastoFibroTest [E-FT]) is proposed, which uses an improved definition of stage F4 (cirrhosis), on the basis of strong clinical criteria. TAGS methods were applied to assess the possible benefit of the new algorithm.

Furthermore, the inventor developed a method making it possible to improve existing diagnosis tests for diseases where no gold standard exists. This method is in particular very interesting for diseases where the patient may present multiple clinical stages (linked to the development of the disease), and where the classification of the patient according to said clinical stages is difficult, in the absence of a gold standard.

In particular, this method of improving diagnosis test is interesting, where there is a continuum in the disease development, with some uncertainty existing when assessing a stage of the disease to a specific patient.

It is reminded that a diagnosis (or diagnostic) method comprises
  i. a step of gathering information from the patient
  ii. a step of comparing said information with regards to thresholds
  iii. a step of deducing, from the difference between the patient's information and the threshold, whether the patient has a specific disease or the stage of the patient's disease.

As a matter of illustration
  i. the information that can be gathered from the patient can be gathered directly from the patient (such as images from NMR, scanner, radiography, contrast-enhanced computed tomography), or from a biological sample that has been obtained from a patient (such as urine, blood sample.). The information can be presence (or absence) and level of specific biological markers, whether specific from the pathogenic determinant (bacterial or viral DNA), or elevated levels of patient's markers
  ii. once the information is obtained, it is compared to different values/standards and the deviation with regards to these standards is assessed. As a matter of illustration, the level of some biomarkers shall be compared to the level usually observed in healthy patients and to the levels usually observed in patients with the disease. Thresholds may exist, where 95% of patients having passed the threshold have the disease and 95% of the patients not having passed the threshold do not have the disease. For diseases where multiple clinical stages can be determined, such thresholds can discriminate the different stages iii. the last step is actually making the diagnosis, taking, in particular, into account the information gathered from the patient, the thresholds as described above. The physician may also take into account other elements (such as the consistency of the information gathered or the like) to make the diagnostic.

The invention thus relates to a method for developing a diagnosis test for diagnosing a specific health condition in the absence of a gold-standard test comprising:
  a) performing one existing diagnosis test on a large number of patients during a first period of time and classifying said patients into disease classes (corresponding to disease development stages) according to the results of said existing diagnosis test
  b) recording all events arising to said patients during a second period of time, wherein said events are linked to said health condition
  c) reassessing the classification of the patients after said second period of time, in order to identify the patients which were wrongly classified during said first period of time
  d) modifying the parameters (such as the parameters to take into account or the threshold for parameters) of said existing diagnosis test in order to take into account the patients that were wrongly classified in the first period of time, thereby developing a new diagnosis test, with increased sensitivity and/or sensitivity with regards to said existing diagnosis test.

The invention thus relates to a method for developing a diagnosis test for diagnosing a specific health condition in the absence of a gold-standard test comprising:
  a) performing multiple existing diagnosis test on a large number of patients during a first period of time and classifying said patients into disease classes (corresponding to disease development stages) according to the results of said existing diagnosis tests
  b) recording all events arising to said patients during a second period of time, wherein said events are linked to said health condition
  c) reassessing the classification of the patients after said second period of time, in order to identify the patients which were wrongly classified during said first period of time
  d) combining said existing diagnosis tests into a new diagnosis test, which takes into account the patients that were wrongly classified in the first period of time, and which presents increased sensitivity and/or sensitivity with regards to said existing diagnosis tests.

In particular, said method is used for diseases where no gold standard exists.

It is also usable for diseases presenting a continuum of disease evolution.

It is also usable for diseases presenting different clinical stages of disease evolution.

In particular, the invention relates to a method for developing an in vitro diagnostic test for diagnostic of liver fibrosis, comprising the step of:
  1) measuring the values of the concentration of biochemical markers in the blood or serum on a large group of patients, during a first period of time, and combining said values through a first logistic function in order to obtain a first end value,
  2) optionally measuring liver stiffness on said patients in order to obtain a second end value
  3) classifying said patients according to the METAVIR score, according to the results of said existing diagnosis tests
  4) recording events arising to said patients during a second period of time, wherein said events are linked to evolution of liver disease
  5) reassessing the classification of the patients having suffered said events, in order to after said second period of time, so that the patients having suffered said events are classified as METAVIR F4 if they had been classified as METAVIR F0, F1, F2 or F3 in step 3)
  6)
     a. modifying the parameters of the first logistic function of step 1 in order to develop a modified first logistic function, and/or
     b. designing a new logistic function using the first end value of said first logistic function (whether modified according to a) and the second end value obtained after liver stiffness measurement
  thereby developing a new diagnosis test, with increased sensitivity and/or sensitivity for diagnostic of liver fibrosis.

In the method as above, the logistic function of steps 1) and 6.a) are obtained by
  i) classification of the patients in different groups according to the extend of their disease (in particular according to the METAVIR score obtained from liver biopsy for the first logistic function of step 1), the METAVIR score obtained by running the first logistic function and reassessing the patients having suffered adverse events in step 6));
  ii) identification of factors which differ significantly between these groups by unidimensional analysis;
  iii) logistic regression analysis to assess the independent discriminative value of markers for the diagnosis of fibrosis and/or liver necroinflammatory lesions;
  iv) construction of a new logistic function by combination of these identified independent factors, and The art already describes different means making it possible to obtain a logistic function, the end vale of which is indicative of the degree of liver fibrosis. In particular, one can cite WO 2002/016949, and different declinations of the method first described in WO 2002/016949: WO 2010/149767, WO 2006/10357, WO 2006/082522, WO 2003/073822, WO 2011/039321, WO 2005/116901, WO 2010/058295, WO 2010/097472.

According to step 1) above, a "large number of patients" is to mean more than 50 patients, preferably more than 100 patients, preferably more than 200 patients, more preferably more than 500 patients.

According to step 4) above, the second period of time starts, for each patient, after step 1) and optionally step 2) have been performed. The second period of time lasts (for each patient) preferably more than 1 year, more preferably more than 2 years, more preferably more than 3 years, more preferably about 5 years. The second period of time is preferably less than 6 years.

Adverse events recorded in step 4) are such as liver-related death, liver transplantation, episode of ascites or presence of esophageal varices at endoscopy. Presence of these adverse events in the second period of time indicates that the METAVIR state of the patient was F4.

In step 6.b), the logistic function is obtained by logistic regression using the end value of said first logistic function (whether modified according to a) and the second end value obtained after liver stiffness measurement. This method is standard in the art and different functions can be obtained depending on the METAVIR stage taken into account (F2F3F4, or F4).

In step 2), said second end value may be the logarithmic (Log also written as L) value of the measured liver stiffness.

In a preferred embodiment, the first logistic function is Fibrotest® as described below.

In a preferred embodiment, liver stiffness is measured, in particular by Fibroscan®, as described below.

In a preferred embodiment, step 6.a) is not performed (i.e. the new diagnostic test is developed by combination of the first logistic function and of the liver stiffness measurement, without modifying the first logistic function.

It is to be noted that improving the detection of cirrhosis (the method as described above makes it possible to reclassify patients as cirrhotic, where they were not identified as such in the first place) leads to a globally improved test, even for classification of patients that are classified as <F4 in the METAVIR classification.

The inventor has applied the above method for improving the in vitro diagnostic of liver fibrosis, and specifically liver cirrhosis.

As indicated above, biopsy can not be considered to be a gold standard test, as the biopsy may not contain all interesting information, and as various pathologists looking at the slide of tissues may have different interpretation of the stage of development of the fibrosis.

The liver fibrosis is assessed according to the METAVIR score (F0, no damages to F4, cirrhosis), where patients needing to be treated present a METAVIR scores≥F2.

The inventor has used a cohort of patients, in which Fibrotest®, Fibroscan®, liver biopsy were performed. The patients were initially classified according to the results obtained from the different tests.

After a follow-up of a few years, adverse events (liver-related death, or other liver-related events) were assessed. These events would only have been expected from patients classified as METAVIR F4.

It was thus possible to re-classify patients, initially considered to be F3 or F2, as F4 patients.

The inventor then designed a function which combines the Fibrotest® and Fibroscan® tests. This new function (ElastoFibrotest™) presents a higher specificity and sensitivity than Fibrotest® and Fibroscan® for detecting F4 patients.

The Fibrotest® combines five markers: alpha2-macroglobulin, haptoglobin, apolipoprotein A1, total bilirubin and gamma-glutamyl transpeptidase (GGT), and adjusts with sex and age. The algorithm for Fibrotest® reads as follows: $4.467 \times Log(Alpha2Macroglobulin\ (g/l)) - 1.357 \times Log(Haptoglobin\ (g/l)) + 1.017 \times Log(GGT\ (IU/l)) + 0.0281 \times Age\ (in\ years) + 1.737 \times Log(Bilirubin\ (\mu mol/l)) - 1.184 \times ApoA1\ (g/l) + 0.301 \times Sex\ (female=0,\ male=1) - 5.540$. It is protected by US and European patents from Assistance Publique Hôpitaux de Paris, and licensed to Biopredictive.

It is performed in vitro on a biological sample (blood or serum) that has been harvested from a patient.

The Fibroscan® measures liver stiffness by Vibration Controlled Transient Elastography. Briefly, a single element ultrasound transducer is mounted on the axis of the vibrator. The vibration consists in a period of sinusoid with a frequency of 50 Hz and a 2 mm peak-to-peak amplitude. The vibration therefore lasts only 20 ms. The speed of propagation of the vibration is measured by the ultrasound transducer and depends on the stiffness of the organ through which it passes. The measurement obtained is used to quantify the stiffness of the liver: the stiffer it is (fibrous), the faster the vibration propagates.

Liver stiffness measurement (LSM) is usually performed with the patient lying in dorsal decubitus with the right arm in maximal abduction, on the right lobe of the liver, through intercostal spaces. The operator, assisted by a time-motion ultrasound image, should locate a liver portion at least 6-cm thick and free of large vascular structures. When the target area is located, he presses the probe button to commence the measurements.

Using the M probe of FibroScan, the measurement depth is between 25 and 65 mm. Multiple (usually around ten) validated measurements are performed on each patient. Results are expressed in kilopascals (kPa). Only procedures with at least 10 validated measurements, at least 60% of success rate and an interquartile range<30% of the median value are considered reliable.

Castera et al (Gastroenterology 2005; 128:343-350) have described that combined use of FT and LS could be used reliably for first-line pre-therapeutic evaluation of fibrosis in HCV-infected patients, and that this could avoid LB examination in most patients with Chronic Hepatitis C. In this article, combination is intended to mean performing both methods and compare the results for each method.

Vergniol et al (Gastroenterology 2011; 140:1970-1979) have described the follow-up of patients overtime, and assessed the prognosis ability of Fibrotest® and Fibroscan®.

The invention thus relates to an in vitro method for diagnosis of liver cirrhosis in a patient comprising the steps of:

a) measuring the values of at alfa2-macroglobulin, haptoglobin, apolipoprotein-A1, total bilirubin, gamma-glutamyl-transpeptidase (GGT) in the serum or plasma of said patient, and combining said values through a first logistic function including said markers, the age and sex of said patient, wherein said first logistic function is $4.467 \times Log(Alpha2Macroglobulin\ (g/l)) - 1.357 \times Log(Haptoglobin\ (g/l)) + 1.017 \times Log(GGT\ (IU/l)) + 0.0281 \times Age\ (in\ years) + 1.737 \times Log(Bilirubin\ (\mu mol/l)) - 1.184 \times ApoA1\ (g/l) + 0.301 \times Sex\ (female=0,\ male=1) - 5.540$, and obtaining a first index b) measuring liver stiffness for said patient by Vibration Controlled Transient Elastography and obtaining a second index c) combining said first and second index through a second logistic function in order to obtain a final index, wherein said second logistic function is $a1 + a2 \times [first\ index] + a3 \times [second\ index]$ wherein a1 is comprised between −9.27 and −9.07; a2 is comprised between 3.08 and 3.1; a3 is comprised between 5.67 and 5.87.

In this embodiment, the second logistic is named EFT-F4.

In a preferred embodiment, said second logistic function is $-9.1753 + 3.0893 \times [first\ index] + 5.7786 \times [second\ index]$.

In another embodiment, the invention relates to an in vitro method for diagnosis of advanced liver fibrosis in a patient comprising the steps of:

a) measuring the values of at alfa2-macroglobulin, haptoglobin, apolipoprotein-A1, total bilirubin, gamma-glutamyl-transpeptidase (GGT) in the serum or plasma of said patient, and combining said values through a first logistic function including said markers, the age and sex of said patient, wherein said first logistic function is $4.467 \times Log(Alpha2Macroglobulin\ (g/l)) - 1.357 \times Log(Haptoglobin\ (g/l)) + 1.017 \times Log(GGT\ (IU/l)) + 0.0281 \times Age\ (in\ years) + 1.737 \times Log(Bilirubin\ (\mu mol/l)) - 1.184 \times ApoA1\ (g/l) + 0.301 \times Sex\ (female=0,\ male=1) - 5.540$, and obtaining a first index b) measuring liver stiffness for said patient by Vibration Controlled Transient Elastography and obtaining a second index c) combining said first and second index through a second logistic function (EFT-F2) in order to obtain a final index, wherein said second logistic function is $b_1+b_2\times$[first index]$+b_3\times$[second index] wherein $b_1$ is comprised between 2.35 and 2.55; $b_2$ is comprised between 2.8 and 3; $b_3$ is comprised between 2.25 and 2.45.

In this embodiment, the second logistic function is named EFT-F2.

In a preferred embodiment, said second logistic function is $2.4518+2.8935\times$[first index]$+2.3657\times$[second index].

This new diagnosis tests are very valuable for the physicians. Indeed, using the EFT-F4 function would make it possible to strengthen the diagnostic of liver cirrhosis, and obtain better results than the ones obtained using Fibrotest®, Fibroscan® or liver biopsy alone. This is of particular importance as patients with cirrhosis (METAVIS F4) shall receive the appropriate treatment.

In particular, the new algorithm EFT-F4 designed by the inventor has increased specificity and sensitivity for detecting liver cirrhosis, with regards to the existing tests.

Figure 1:
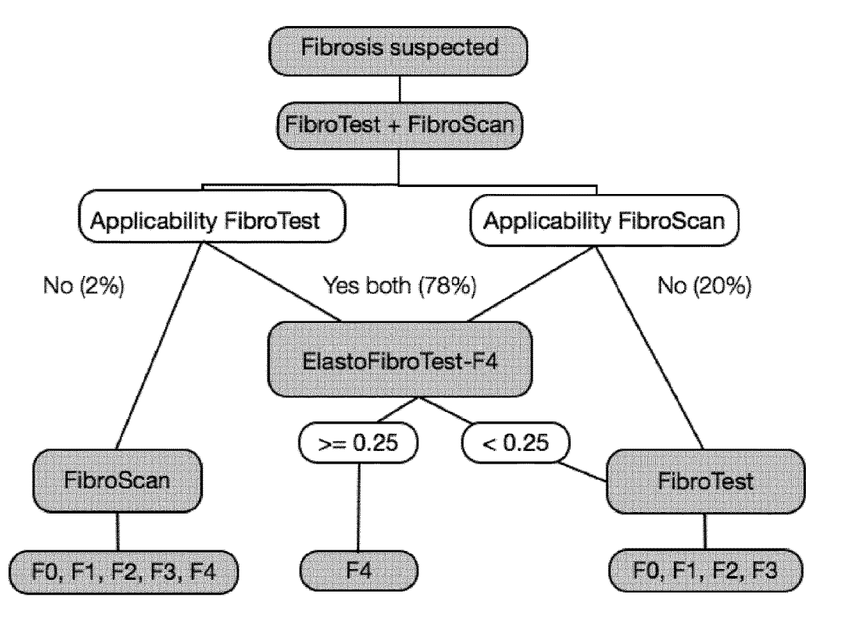

In particular, it is foreseen that the physician shall:
i. obtain the data from the Fibrotest®, Fibroscan® and ElastoFibrotest™ (EFT-F4)
ii. use the EFT-F4 result if it is above the threshold for F4
iii. use the Fibrotest® data to assess the degree of fibrosis is the EFT-F4 result is below the threshold As indicated in FIG. 1, the physician shall use only the Fibrotest® result of the Fibroscan® data is not usable (about 20% of case), and only the Fibroscan® result if the Fibrotest® result is not applicable. If both tests give non-usable results, a liver biopsy or another validated fibrosis biomarker test shall be performed.

Thus, the invention relates to a method for determining the level of liver fibrosis in a patient comprising the steps of
a) Performing the method as described above, in order to obtain the result for the EFT-F4 function as the second logistic function
b) Assessing the METAVIR F4 stage to the patient if the result of said second logistic function is higher or equal to 0.25
c) If the result of said second logistic function is lower than 0.25, assessing the stage of fibrosis of said patient using the Fibrotest®

"Advanced fibrosis" (METAVIR F2 or F3) state is assigned to said patient if the Fibrotest® result is higher or equal to 0.48, or and "no or low fibrosis" state (METAVIR F0 or F1) is assigned to said patient if the Fibrotest® result is lower than 0.48.

The invention also relates to a method usable in a diagnostic method for determining the level of liver fibrosis in a patient comprising the steps of
a) measuring the values of at alfa2-macroglobulin, haptoglobin, apolipoprotein-A1, total bilirubin, gamma-glutamyl-transpeptidase (GGT) in the serum or plasma of said patient, and combining said values through a first logistic function including said markers, the age and sex of said patient, wherein said first logistic function is $4.467\times$Log(Alpha2Macroglobulin (g/l))$-1.357\times$Log(Haptoglobin (g/l))$+1.017\times$Log(GGT (IU/l))$+0.0281\times$Age (in years)$+1.737\times$Log(Bilirubin (μmol/l))$-1.184\times$ApoA1 (g/l)$+0.301\times$Sex (female=0, male=1)$-5.540$, and obtaining a first index
b) measuring liver stiffness for said patient by Vibration Controlled Transient Elastography and obtaining a second index c) if methods of a) and b) give an interpretable result, combining said first and second index through a second logistic function in order to obtain a final index, wherein said second logistic function is $-9.1753+3.0893\times$[first index]$+5.7786\times$[second index].

Said method makes it possible to finalize a diagnostic
If step c) has been performed,
1) determine that the liver of the patient is METAVIR F4 if the final index is higher or equal to 0.25
2) determine the stage of liver fibrosis of said patient using the first index if said final index is lower than 0.25, If step c) has not been performed, (if one method of a) or b) gives an non-interpretable result), use the index obtained for the other method in order to determine the level of liver fibrosis in said patient The two above methods are in vitro methods. These two methods are applied to patients in whom the Fibrotest® and/or the Fibroscan® give an interpretable result.

The method of the invention can also be used as a predictive mean for the evolution of the disease. In particular, when the patient is infected with the hepatitis C virus, it is often possible to determine the date of the infection (usually through transfusion). Therefore, the use of the method of the invention to determine the degree of evolution of the disease through the date of the diagnosis can also allow for the prognosis of the future development of the disease.

The data obtained by the diagnosis method according to the invention can also be very valuable for the physician to choose a suitable treatment for the patient, according to the stage of the disease.

Repeating the method of the invention on a regular basis also makes it possible to determine the efficiency of a treatment.

The method of the invention is intended to be used for patient suffering of liver fibrosis, which could develop to cirrhosis. In particular, the method of the invention is advantageously performed for detecting liver fibrosis in patient suffering form a disease included in the group consisting of hepatitis B and C, alcoholism, hemochromatosis, metabolic disease, diabetes, obesity, autoimmune hepatitis, primary biliary cirrhosis, alpha1-antitrypsin deficit, Wilson disease.

The method of the invention is best performed on patients infected with a hepatitis virus, in particular the hepatitis C virus.

The invention is also drawn to a kit of diagnosis of liver fibrosis and/or liver cirrhosis in a patient, comprising instructions allowing to determine the presence of liver fibrosis and/or liver cirrhosis lesions in said patient, after dosage of the biochemical markers, and measurement of liver stiffness.

The instructions comprise the two logistic functions that has to be used after determination of the dosage of the biochemical markers and in order to combine the result of the Fibrotest® and the Fibroscan®. It can appear as a printed support as well as a computer usable support, such as a software. The instructions may also comprise the threshold and tables that permit to obtain the predictive values, depending of the expected prevalence of fibrosis in the patient population.

The following examples are meant to describe an aspect of invention, but shall not be limiting the invention.

DESCRIPTION OF THE FIGURE

FIG. 1: summary of the algorithm to combine Fibrotest® and LSM for

EXAMPLES

Materials and Methods

Methods

Patients

An integrated database previously described [13] was used including 1,893 subjects: three populations of patients with CHC (n=1289), and one population of apparently healthy volunteers (Healthy cohort, n=604).

To be included, patients had to have chronic hepatitis C, be PCR positive, and have the results of liver biopsy, FibroTest, LSM, interpretable according to the usual recommendations and precaution of use. In all these cohorts, each of the tests were performed without knowledge of the three others.

The group of 604 healthy volunteer subjects without any risk of liver disease was analyzed in order to define the specificity of each test, as the probability of true advanced fibrosis was very low.

The inclusion criteria were: no liver disease history, no or low alcohol consumption (≤10 g/day for females, ≤20 g/day for males), HBsAg negative, HCV antibodies negative, and interpretable Fibrotest® and LSM results. As it was not possible to perform liver biopsy in these healthy volunteers, we used large surgical biopsies obtained from four subjects without liver disease. From the digitized image of the whole section, 626 virtual biopsy specimens of 20 mm length were produced [13].

Obtention of Virtual Biopsies

As it was not possible to perform liver biopsy in healthy volunteers, large surgical biopsies were obtained from four patients (3 males, 1 female, age range 40-68 years) without liver disease history, normal Fibrotest® results (range 0.13-0.26) and normal LSM (range 4.4–5.6 kPa).

The whole section of each surgical specimen was stained in the pathology unit. From the digitized image (Aperio Scanner, TRIBVN, France) of the whole section, virtual biopsy specimens of increasing length were produced.

For the present study, 626 biopsy specimens of 20 mm lengths were assessed. Each such specimen with the prevalence of false positive was then assigned randomly to each of the 626 healthy control volunteers.

Advanced fibrosis (METAVIR F2) was assigned to samples with presence of fibrotic regions on more than >5.3% of the surface of the sample.

Cirrhosis (METAVIR F4) was assigned to samples with presence of fibrotic regions on more than >16.5% of the surface of the sample.

The >5.3% threshold corresponds to the upper limit of 95% confidence interval of the mean area of fibrosis equivalent to METAVIR stage F2 and >16.5% the lower limit of 95% confidence interval of the mean area of fibrosis equivalent to METAVIR stage F4, obtained in 5 patients (2909 virtual biopsies 20 mm length) with chronic hepatitis C on large surgical specimens (Poynard 2010). These thresholds were closed to those observed by Bedossa et al (Hepatology 2003) for F2 and F4.

TABLE 1

Correspondence between area of fibrosis as assessed by image analysis (reference value) in whole sections and METAVIR Stage

| | | Area of Fibrosis by Image Analysis | | |
|---|---|---|---|---|
| METAVIR Stage | Number virtual biopsies of 20 mm | Present study | | Bedossa, 2003 |
| | | Mean (95% CI) | Range | Range |
| F0 | 626 | 3.8 (3.5-4.0) | 0.0-34.4 | 1.8-2.2 |
| F1 | 137 | 5.0 (4.5-5.3) | 1.3-13.9 | 3.1-3.6 |
| F2 | 768 | 7.1 (8.0-8.5) | 0.9-36.4 | 5.4-7.0 |
| F3 | 270 | 9.1 (7.9-10.1) | 0.0-76.4 | 13.5-15.8 |
| F4 | 1734 | 18.2 (16.5-17.6) | 0.3-74.8 | 23.9-27.3 |

Fibrotest®

Fibrotest® was performed according to published recommendations [17]. The following usual recommended cutoffs were used to estimate the presumed fibrosis stages: 0.48, and 0.74 for the F2 and F4 staging, respectively.

Liver Stiffness Measurements

Patients were studied using transient elastography (M probe, Fibroscan® EchoSens Paris). The LSM results are expressed in kilopascals (kPa). Measurements were performed on the on the right lobe of the liver, through intercostal spaces with the patient lying in dorsal decubitus with the right arm in maximal abduction. The tip of the transducer probe was covered with coupling gel and placed on the skin, between the rib bones at the level of the right lobe of the liver.

The operator, assisted by a time-motion ultrasound image, located a liver portion at least 6-cm thick and free of large vascular structures. When the target area had been located, the operator pressed the probe button to commence the measurements. The measurement depth was between 25 and 65 mm.

Ten validated measurements were performed on each patient. The success rate was calculated as the number of validated measurements divided by the total number of measurements. The results were expressed in kilopascals (kPa). The median value was considered representative of the elastic modulus of the liver.

For LSM reliability, the recommended criteria were a success rate greater than 60%, at least 10 valid LSM and interquartile range/median LSM<30% [10]. The following usual recommended cutoffs were used to estimate the presumed fibrosis stages: 8.8, and 14.5 kPa for the F2, and F4 staging, respectively [10, 18, 19].

Biopsy Among Patients with Chronic Hepatitis C

Staging and grading were performed blinded to the non-invasive methods. In all groups, liver biopsies were performed with a 1.6 mm needle (Hepafix, Brown, Melsungen, Germany), and were formalin-fixed and paraffin embedded. Sections (4 mm) were stained with hematoxylin-eosin-saffron and picrosirius red. The liver fibrosis stage was evaluated according to the METAVIR scoring system [20].

Design and Modeling

Concepts

The previous concepts of TAGS method (Latent class with random effect [LCM-R]) and the use of a control population with virtual biopsies have been detailed previously [13]. Two new concepts were used in the present study.

First, an algorithm combining Fibrotest® and LSM, derived from an improved definition of cirrhosis using clinical strong endpoints, was generated. Patients with a standard diagnosis of not cirrhotic stage by biopsy (stage METAVIR F0/F1/F2/F3) were re-classified as cirrhosis (F4) if, in less than 5 years, they died of a complication of cirrhosis, or have been transplanted, or had an episode of ascites or presence of esophageal varices at endoscopy.

The second concept was to use same set of reference tests (biopsy, ALT (Alanine Aminotransferase) and age) in two separate LCM-R models in order to compare the improvement of EFT-F2 or EFT-F4 versus isolated FT and LSM, without violating the assumption of independency between tests if EFT was directly combined with FT and LSM.

Basic Model

Four different tests (i.e, FibroTest, LSM, ALT and biopsy) were applied in all patients, with each test producing a dichotomous test result (e.g. the test was either positive or negative). None of these tests was error-free.

For a single test, the probability of obtaining a positive test result could be written as the sum of finding a positive test in a patient who has fibrosis and a positive test result in a patient without fibrosis. These probabilities can be written as a function of the following unknown measures: prevalence, sensitivity and specificity of the test. Therefore nine parameters were unknown in this model: one prevalence parameter and the sensitivity and specificity for each of the four tests.

With four different dichotomous tests, there were 16 possible combinations. By using the probabilities for a positive or negative test result, the likelihood of observing each pattern of test results could be calculated. The number of subjects for each of the 16 patterns of test results was observed. For the control group virtual biopsies were used as described above [13].

For each 8 possible combinations of FibroTest, LSM and ALT results (fibrosis present or absent) the number of virtual biopsy results (fibrosis present or absent) was calculated by multiplying the number of subjects in each 8 possible combinations by the mean prevalence of fibrosis observed using large surgical biopsies from normal livers. In other words, analysis of the virtual biopsy samples obtained from the large biopsies from normal livers made it possible to determine the percentage of said virtual biopsies being classified as F2 or as F4 (these being false positive). Such percentage were then used for the patients in each of the 8 possible combinations as mentioned above.

This method thus permitted to generate the 16 distributions of subjects according to the four tests' results (Table 2). Thereafter, the standard maximum likelihood methods could be used to obtain a (unique) solution by latent class analysis [9, 12-13, 21-23].

TABLE 2

Distribution of 1893 subjects according to the 16 possible combinations of the 4 tests' results: presumed advanced fibrosis (present = 1) or not (absent = 0)

| Type of combination (n = 16) | | | | Number of subjects | |
|---|---|---|---|---|---|
| FibroTest | LSM | ALT | Biopsy | Observed | Expected by the latent class model |
| 0 | 0 | 0 | 0 | 621 | 615.5 |
| 0 | 0 | 0 | 1 | 186 | 191.1 |
| 0 | 0 | 1 | 0 | 190 | 197.5 |
| 0 | 0 | 1 | 1 | 123 | 117.4 |
| 0 | 1 | 0 | 0 | 10 | 10.0 |
| 0 | 1 | 0 | 1 | 18 | 18.4 |
| 0 | 1 | 1 | 0 | 18 | 16.4 |
| 0 | 1 | 1 | 1 | 39 | 39.2 |
| 1 | 0 | 0 | 0 | 41 | 47.0 |
| 1 | 0 | 0 | 1 | 58 | 54.8 |
| 1 | 0 | 1 | 0 | 95 | 86.6 |
| 1 | 0 | 1 | 1 | 141 | 145.1 |
| 1 | 1 | 0 | 0 | 9 | 8.3 |
| 1 | 1 | 0 | 1 | 45 | 43.1 |
| 1 | 1 | 1 | 0 | 23 | 25.7 |
| 1 | 1 | 1 | 1 | 276 | 277.0 |

Latent Class Analysis

Latent class uses the standard maximum likelihood method to combine the test results from each patient for constructing a reference standard [12, 21-23]. This reference standard estimates for each test sensitivities and specificities compatible with the observed 16 distributions. This method acknowledges that there is no gold standard and that the available tests are all related to the unknown true status: fibrosis present or absent. These unobservable outcomes are named latent classes.

The fact that a two-class model might not fit the data is either seen as an artifact of the measurement instrument or as a result of within-class heterogeneity. To allow for local dependencies and within-class heterogeneity, a LCM model with a random-factor, the LCM-R model [12, 21-23] was used. The LCM-R model incorporates random effects and thus relaxes the conditional independence assumption.

The specific assumptions for random effects were the following: there was dependency between tests for Fibrotest® and LSM which were initially validated by biopsy; the intra-class heterogeneities for biopsy was due to inter-observers variability and sampling error; for LSM, the heterogeneity was due to inter-observers variability and the impact of inflammation and steatosis.

In LCM-R, it is assumed that the outcome of a diagnostic test is governed by two mechanisms or factors: the disease status of the subject, and the individual's biological process or the diagnostic test's technological characteristics.

In the present study each LCM-R model included three tests: the test to evaluate (successively FibroTest®, LSM, EFT-F2 and EFT-F4), and two permanent tests: biopsy and ALT. The cutoffs used for the diagnosis of F234 and for F4 were the standard recommended cutoffs [13]. Models using LCM-R were interpretable when they fit the observed distribution of tests' results. The fit was reached when the likelihood ratio goodness of fit value (likelihood squared $[L^2]$) $L^2$ significance was superior to 0.05 [12,21-23]. If the fit was not reached, no LCM-R was provided and the performances of tests cannot be estimated.

This latent class analysis made it possible to determine the nine unknown parameters as specified above: prevalence, sensitivity and specificity for each of the four tests.

Sources of Fit Impairment

The inventor assessed which tests' dependency or heterogeneity significantly impaired the fit of the standard LCM without random effects by using bivariate residuals of the baseline latent class analysis. The pair of tests were excluded step by step up until a model which fit the observed results was obtained. The fit was reached when the likelihood-ratio goodness-of-fit value [likelihood squared $(L^2)$] $L^2$ significance was >0.05 [12, 21-23].

Standard Performance Analysis Using Biopsy as a Gold-standard

The standard performances of tests (EFT-F2, EFT-F4, FibroTest, LSM were assessed using the fibrosis stage obtained by liver biopsy, the classical gold standard, expressed using the METAVIR scoring system. The thresholds for test positivity were the usual ones. The standard area under the Receiver Operating Characteristics Curves (AUROC) was estimated by the empirical (non-parametric) method, and compared using the paired method of Zhou et al. [24].

The Obuchowski measure was used to take into account all the pairwise comparisons between stages to minimize the spectrum effect and the risk of multiple testing [25]. In brief, for a given test, Obuchowski measures the AUROC for the test for assessing all pairwise comparisons conditions (being F0, F1, F2, F3, F4), the Obuchowski measure being the average of each obtained value.

Statistical Analysis and Software

NCSS software (Kaysville, Utah, USA) [26] was used for standard statistics and LatentGold-4.5 software (Statistical Innovation, Belmont, Mass., USA) for estimating the model parameters [23]. We used the following criteria to identify a good model: the p-value of the likelihood squared ($L^2$) had to be greater than 0.05, and the Bayesian information criterion (BIC), defined as $L^2 - \log(N) \times Df$ (degrees of freedom of the data), had to be the smallest among all competing models. Standard error of $L^2$ was calculated used bootstrap method [23].

The study was conducted according to the principles expressed in the declaration of Helsinki. Signed informed consents were obtained for all controls and for patients for whom tests were not routinely performed according to the standard of care.

Results

Subjects Included

The characteristics of included HCV patients were usual, 25% with cirrhosis presumed by biopsy, 56% male and median age 49 years old. Healthy controls were less often female (44%) and older (58 years) than HCV patients (Table 3). The median length of biopsy was 17 mm in the training group (779 patients), and 23 mm in validation group (510 patients). Failure and non-reliable results were observed in 15.3% (525/3441) of LSM and in 0.6% for Fibrotest® (20/3441).

TABLE 3

Characteristics of the 1,893 included subjects according to groups

| | HCV Patients' group | | | Healthy |
|---|---|---|---|---|
| Characteristic | Training n = 779 | Validation n = 510 | All patients n = 1,289 | Volunteers n = 604 |
| Age year[1] | 48 (47-49) | 50 (49-51) | 49 (48-50) | 58 (56-59) |
| Male (%) | 464 (60%) | 292 (57%) | 728 (56%) | 209 (44%) |
| Biopsy stage[2] | 2 (2-2) | 1 (1-2) | 2 (2-2) | 0 (0-0) |
| Presumed fibrosis | 506 (65%) | 241 (47%) | 747 (58%) | 16%[3] |
| Presumed cirrhosis | 206 (26%) | 119 (23%) | 325 (25%) | 3%[3] |
| Fibrotest® | 0.53 (0.49-0.57) | 0.62 (0.54-0.65) | 0.55 (0.53-0.59) | 0.16 (0.15-0.16) |
| Presumed fibrosis | 423 (54%) | 311 (61%) | 734 (57%) | 19 (3%) |
| Presumed cirrhosis | 222 (29%) | 177 (35%) | 399 (31%) | 2 (0.3%) |
| LSM kPa (8.8/14.5) | 7.7 (7.3-7.8) | 7.8 (7.4-8.3) | 7.8 (7.4-8.0) | 5.4 (3.6-6.7) |
| Presumed fibrosis | 312 (40%) | 214 (42%) | 526 (41%) | 19 (3%) |
| Presumed cirrhosis | 172 (22%) | 114 (22%) | 286 (22%) | 2 (0.3%) |
| ALT IU/L | 79 (74-86) | 83 (77-86) | 81 (77-85) | 22 (21-23) |
| Presumed fibrosis | 554 (71%) | 384 (75%) | 938 (73%) | 23 (4%) |
| Presumed cirrhosis | 274 (35%) | 180 (35%) | 454 (35%) | 4 (0.7%) |

[1]Median (95% confidence interval)
[2]METAVIR scoring system
[3]False positive of a 20 mm length biopsy as assessed using large surgical specimens EFT Training and Validation A total of 768 patients with all prognostic data out of the 779 patients of the training population were included for the new definition of cirrhotic stage (F4) [27]. Blindly to biomarkers, the definition of F4 definition was changed in 11 patients due to the occurrence of five deaths related to cirrhosis complications, eight oesophageal varices and two ascites, with more than one complication in three cases (Table 4).

TABLE 4 characteristics of patients with a revised stage of cirrhosis the reference

| Number | Initial stage | Revised stage | FT | LSM | Death | Death Liver | Ascites | Varices |
|---|---|---|---|---|---|---|---|---|
| 1 | F2 | F4 | 0.52 | 15.9 | yes | yes | no | no |
| 2 | F3 | F4 | 0.96 | 45.0 | yes | yes | no | yes |
| 3 | F2 | F4 | 0.72 | 43.6 | no | no | no | yes |
| 4 | F2 | F4 | 0.52 | 8.8 | yes | no | no | yes |
| 5 | F3 | F4 | 0.93 | 15.1 | no | no | no | yes |
| 6 | F3 | F4 | 0.89 | 17.3 | no | no | no | yes |
| 7 | F3 | F4 | 0.98 | 75.0 | yes | yes | yes | yes |
| 8 | F2 | F4 | 0.99 | 35.5 | yes | yes | no | no |

TABLE 4-continued characteristics of patients with a revised stage of cirrhosis the reference

| Number | Initial stage | Revised stage | FT | LSM | Death | Death Liver | Ascites | Varices |
|---|---|---|---|---|---|---|---|---|
| 9 | F2 | F4 | 0.55 | 7.7 | yes | yes | no | yes |
| 10 | F3 | F4 | 0.95 | 41.6 | no | no | no | yes |
| 11 | F2 | F4 | 0.59 | 24.3 | no | no | yes | no |

The best combination for F234 (advanced fibrosis, F2) was EFT-F2=−2.4517+2.893×Fibrotest+2.3656×Lfibroscan), producing an AUROC=0.864 (0.013) [mean (se)] and Obuchowski=0.881 (0.005). The odds ratio (95% Cl) were for Fibrotest®=18.1 (8.0–41.0) and LSM=10.7 (3.8–30.2).

The best combination for F4 was EFT-F4=−9.1753+3.089×Fibrotest+5.7785×LFibroscan producing an AUROC=0.914 (0.010) [mean (se)] and Obuchowski=0.885 (0.005). The odds ratio (95% Cl) were for Fibrotest®=22.0 (5.8–83.3) and LSM=323.3 (93.0–1124.1).

Validation of EFT by Standard Methods

The AUROCs and Obuchowski of EFT-F2 and EFT-4 were similar in the validation population in comparison with training population, and in the overall population of patients (n=1289). Among all patients, the AUROCs were 0.867 and 0.921, the Obuchowski measures 0.875 and 0.892, for EFT-F2 and EFT-F4 respectively (Table 5).

TABLE 5

Training and validation of EFT-F2 and EFT-F4

|  | Training n = 779 | Validation n = 510 | All patients n = 1289 |
|---|---|---|---|
| ElastoFibroTest-F2 | | | |
| AUROC for F234[1] | 0.864 (0.013)[2] | 0.924 (0.012)[3] | 0.867 (0.010) |
| Obuchowski (between all stages) | 0.881 (0.005)[4] | 0.871 (0.005)[5] | 0.875 (0.004) |
| ElastoFibroTest-F4 | | | |
| AUROC for F4[1] | 0.914 (0.010) | 0.938 (0.011)[6] | 0.921 (0.008) |
| Obuchowski | 0.885 (0.005) | 0.907 (0.006)[3] | 0.892 (0.004) |

[1]Stage in METAVIR scoring system: F234 = advanced fibrosis, F4 = cirrhosis
[2]mean (standard error)
[3]P < 0.001 vs training
[4]P = 0.56 vs Obuchowski of EFT-F4
[5]P = 0.0002 vs Obuchowski of EFT-F4
[6]P = 0.02 vs training These performances were increased when healthy volunteers were included in the overall population (n=1893). The AUROCs were 0.919 and 0.950, the Obuchowski measures 0.909 and 0.915, for EFT-F2 and EFT-F4 respectively (Table 6).

TABLE 6

Performance of Elasto-Fibrotest ® for the diagnosis of advanced fibrosis and cirrhosis in the integrated database with healthy volunteers. Quantitative methods using biopsy as a Gold Standard (n = 1893).

| Method | ElastoFibroTest-F2 | ElastoFibroTest-F4 | FibroTest | LSM | Significance EFT (<0.0001) |
|---|---|---|---|---|---|
| Obuchowski | 0.909 (0.002) | 0.915 (0.002) | 0.893 (0.003) | 0.894 (0.003) | vs FT/LSM |
| AUROC F234 | 0.919 (0.005) | 0.946 (0.005) | 0.887 (0.008) | 0.889 (0.006) | vs FT/LSM |
| AUROC F4 | 0.920 (0.005) | 0.950 (0.005) | 0.903 (0.008) | 0.938 (0.006) | vs FT/LSM |

TAGS Evaluation of EFT-F2 and EFT-F4

The cutoff of each presumed stage by EFT were the 95% upper limit for the mean of EFT for the biopsy stage as observed in the training population.

For EFT-F2 the cutoffs were F1=0.50; F2=0.57; F3=0.75; F4=0.79.

For EFT-F4 the cutoffs were F1=0.03; F2=0.07; F3=0.18; F4=0.25.

Assessment of the Specificity of Liver Biopsy Using Large Surgical Biopsies

Specificity refers to the number of false positive for a test. For biopsy, it is calculated as the number of samples that appear to be positive for normal liver.

As indicated above, for the virtual biopsies (arising from normal liver), cases with areas of fibrosis above 5.3% were considered to be false positives for the diagnosis of advanced fibrosis, and those above 16.5% as false positives for the diagnosis of cirrhosis.

Consequently, the specificity of a 20 mm length biopsy for the diagnosis of advanced fibrosis was 83.71% (Table 7).

TABLE 7

Data of 626 virtual biopsies of 20 mm length generated by automated image analysis of large surgical biopsies in 4 subjects without liver fibrosis on the whole surgical sample.

| | Large surgical biopsy without fibrosis | |
|---|---|---|
| Fibrosis stage presumed at biopsy according to area of fibrosis | Number of virtual biopsies | Percentage |
| Advanced fibrosis[1] >5.3% | | |
| No: True negative (specificity) | 524 | 83.71% |
| Yes: False positive (1-specificity) | 102 | 16.29% |
| Total | 626 | 100% |
| Cirrhosis >16.5%[2] | | |
| No: True negative (specificity) | 624 | 99.68% |
| Yes: False positive (1-specificity) | 2 | 0.32% |
| Total | 626 | 100% |

[1]>5.3% is the cutoff for area of fibrosis equivalent to METAVIR stage F2 using virtual biopsies
[2]>16.5% is cutoff for area of fibrosis equivalent to METAVIR stage F4

Assessment of Test Performances in the Absence of a Gold Standard

The distribution of the subjects according to the 16 possible combinations of the four tests results are shown in Table 8 for presuming advanced fibrosis and in Table 9 for cirrhosis.

TABLE 8

Distribution of subjects according to the 16 possible combinations of the 4 tests result presuming advanced fibrosis (=1) or not (=0)

| Type of combination (n = 16) | | | | Number of subjects | |
|---|---|---|---|---|---|
| ALT | EFT-F2 | FibroTest | Biopsy | Observed | Expected by the latent class model |
| 0 | 0 | 0 | 0 | 579 | 580.7 |
| 0 | 0 | 0 | 1 | 103 | 100.3 |
| 0 | 0 | 1 | 0 | 0 | 0 |
| 0 | 0 | 1 | 1 | 0 | 0 |
| 0 | 1 | 0 | 0 | 76 | 76.7 |
| 0 | 1 | 0 | 1 | 37 | 36.6 |
| 0 | 1 | 1 | 0 | 50 | 47.5 |
| 0 | 1 | 1 | 1 | 87 | 89.7 |
| 1 | 0 | 0 | 0 | 155 | 153.8 |
| 1 | 0 | 0 | 1 | 48 | 50.5 |
| 1 | 0 | 1 | 0 | 0 | 0 |
| 1 | 0 | 1 | 1 | 0 | 0 |
| 1 | 1 | 0 | 0 | 66 | 65.0 |
| 1 | 1 | 0 | 1 | 75 | 76.3 |
| 1 | 1 | 1 | 0 | 121 | 123.6 |
| 1 | 1 | 1 | 1 | 495 | 491.9 |

TABLE 9

Distribution of subjects according to the 16 possible combinations of the 4 tests result presuming cirrhosis (=1) or not (=0)

| Type of combination (n = 16) | | | | Number of subjects | |
|---|---|---|---|---|---|
| ALT | EFT-F4 | FibroTest | Biopsy | Observed | Expected by the latent class model |
| 0 | 0 | 0 | 0 | 1075 | 1070.4 |
| 0 | 0 | 0 | 1 | 119 | 120.9 |
| 0 | 0 | 1 | 0 | 58 | 60.7 |
| 0 | 0 | 1 | 1 | 14 | 13.6 |
| 0 | 1 | 0 | 0 | 26 | 25.6 |
| 0 | 1 | 0 | 1 | 34 | 37.6 |
| 0 | 1 | 1 | 0 | 25 | 26.8 |
| 0 | 1 | 1 | 1 | 84 | 80.0 |
| 1 | 0 | 0 | 0 | 168 | 173.0 |
| 1 | 0 | 0 | 1 | 17 | 14.4 |
| 1 | 0 | 1 | 0 | 33 | 29.4 |
| 1 | 0 | 1 | 1 | 2 | 4.0 |
| 1 | 1 | 0 | 0 | 27 | 27.4 |
| 1 | 1 | 0 | 1 | 26 | 23.1 |
| 1 | 1 | 1 | 0 | 59 | 57.3 |
| 1 | 1 | 1 | 1 | 126 | 129.0 |

Assessment of Significant Sources of Impairment in Modeling

As expected in a latent class model without random factor, LSM and Fibrotest® were identified as the two main sources of impairment in LCM models both for advanced fibrosis and cirrhosis. This was expected because LSM and Fibrotest® were combined in the EFT. With exclusion of these residuals the models fitted without using a random factor hypothesis.

According to the applicability rates of Fibrotest® and LSM observed in large cohorts and to the performance of EFT-F4, the best algorithm combining Fibrotest® and LSM (FIG. 1) was to predict fibrosis stage using Fibrotest® alone in 20% of patients with non-applicable LSM and in patients with EFT-F4 lower than 0.25; LSM will predict stage in 2% of patients with non-applicable FibroTest; EFT-F4 will predict cirrhosis when greater or equal 0.25. The prevalence of patients classified by EFT-F4 will depend about the spectrum of patients and can varied from 0 to 78%.

It was previously demonstrated that, using appropriate methods without using a gold standard (TAGS), the isolated performance of Fibrotest® and LSM were similar for the diagnosis of cirrhosis and in favor of Fibrotest® for the diagnosis of advanced fibrosis [13].

In the present study it was demonstrated that a new algorithm combining Fibrotest® and LSM (Elasto-FibroTest) using an improved definition of stage F4 (cirrhosis) permitted to obtain better performance for the diagnostic of cirrhosis (EFT-F4) than isolated Fibrotest® (low sensitivity at the 0.74 cutoff) or isolated LSM (low applicability and low specificity and the 14.5 kPa cutoff). The results confirm that Fibrotest® was more accurate than LSM for the diagnosis of advanced fibrosis [13], as EFTF2 had no better performance for the diagnosis of advanced fibrosis (F234) vs. Fibrotest® alone, mainly due to the high applicability and high sensitivity of FibroTest.

The present study has several methodological advantages in comparison with the five previous studies combining serum biomarkers and LSM [4-8].

In the absence of a perfect gold standard the standard methodology [28] is inappropriate [21, 22] and the interpretation of results are misleading for four reasons.

First, indexes such as the "reliable diagnosis interval" (RDI) [6-8] hypothesized that there is 0% of false positive/negative for the reference. However this reference has 30% of false positive/negative for the correct staging of a 20 mm biopsy when a large surgical biopsy is taken as a gold standard [14]. The RDI is therefore mathematically false as the cutoffs identified for obtaining the 90% negative and predictive values are false and should at least include confidence intervals. Furthermore, the biopsy itself has lower RDI among the intermediate stages F1F2F3 versus large surgical biopsies due both to lower performance between adjacent stages [14] and to the lower concordance between pathologists [15]. The estimated diagnostic accuracies greater than 90% for the diagnosis of advanced fibrosis [8] are mathematically impossible to obtain using biopsy as the reference and standard AUROC [16]. On the contrary when TAGS methods are used, the LCM results for sensitivity and specificity can mathematical reach 100% for the diagnosis of F234. In the present study, using standard method the greater AUROCs for F234 were observed for Fibrotest® which reached un maximum of 0.924 which was suspect of spectrum effect; accordingly the AUROC was reduced to 0.871 when using Obuchowski method. Sensitivity and specificity of Fibrotest® for F234 were above 0.90 using LCR.

Second, as the reference used has false positive and false negative the claims that the association of a biomarker and LSM, is the best combination, and that "new algorithms are more precise and entirely non-invasive" [8] are misleading. In France for example the recommended strategy (standard of care) is already almost non-invasive as one validated biomarker is recommended as first line, then another one if the first is not reliable, and biopsy at third line if all biomarkers are not reliable [19]. To prove that new algorithms are "more precise and more non-invasive" in comparison with approved biomarkers will require independent endpoints such as prognostic studies [27] or methods without gold standard [9,12,13]. One strength of the LCM modeling was the paradigm of latent class, which introduces a risk of false positive or false negative for all fibrosis estimates including biopsy. A frequent critique of biomarkers such as Fibrotest® is the statement that "they cannot be better than biopsy which was the initial reference". The TAGS methods illustrate that is not true. Indeed LCM failed to obtain a model that fit with the observed distribution, without including a "random factor" that is unknown sources of variability not necessary related to the diagnostic performance of tests. As EFT is a combination between Fibrotest® and LSM, the first rational variability factor for EFT was this initial "dependency". Interestingly when the residuals of the pair FibroTest-LSM were excluded, the model fitted without random factor.

Third, in the previous studies authors have not included the applicability rate of the tests included in their algorithms [4-8], which is only 80% for Fibroscan® and therefore reduces proportionally the performance in an "intention to diagnose" analysis [11]. We disagree with the lower applicability rate observed by studies [29, 30], which have not estimated the impact of LSM quality criteria (Success rate, IQR and number of valid measures) using appropriate methods such as Obuchowski measure [11] and strength of concordance [9].

Fourth, the risk of false positive results was greater in these five studies as there was a multiplication of statistical comparisons between combinations of fibrosis stages [4,25], no methods assessing the spectrum effect such as Obuchowski measure or "DANA adjustment" [11,25] and as there were several variations of the same test (i.e.; Fibrometer family) without parallel assessment of the risk of false positive/negative for each variant [31].

Lastly, to construct better algorithm, we used an improved definition of cirrhosis stage, which hypothesized that patients classified F2 or F3 by biopsy and who had severe complications of cirrhosis less than 5 years later had indeed already a cirrhosis at baseline. This hypothesis is in accordance with several validations of FibroTest® as a marker of fibrosis progression [34], and as a predictor of morbidity and mortality [27,33]. We acknowledge that the number of patients who met our new criteria for revised stage of cirrhosis was small (n=11) and that these results should be confirmed on a larger population. However we observed significant changes in the fibrosis spectrum in comparison with the standard biopsy reference as classically recommended [28]: a 5.3% increase of cirrhosis' prevalence in comparison with biopsy, from (from 206 to 217) and a 3.7% decrease of F2F3 (from 300 to 289 patients).

For the first time, the performance of a combination of serum biomarkers Fibrotest® and liver stiffness measurements using FibroScan, for the diagnosis of liver fibrosis, has been assessed using more appropriate methodology, as biopsy is not a perfect reference.

For the diagnosis of cirrhosis the Elasto-Fibrotest® has significantly higher performances than Fibrotest® or Fibroscan® alone, when they are interpretable. No improvement in performance has been observed for the diagnosis of advanced fibrosis vs. Fibrotest® alone, when a method without gold standard was used.

Due to the increase of new serum biomarkers and imaging estimates of liver fibrosis, these methods should increase the quality of future evaluations.

REFERENCES

1. Castera L, Pinzani M. Non-invasive assessment of liver fibrosis: are we ready? Lancet 2010; 375:1419-1420.
2. Nguyen D, Talwalkar J A. Noninvasive assessment of liver fibrosis. Hepatology. 2011; 53:2107-10.
3. Poynard T, First-line assessment of patients with chronic liver disease with non-invasive techniques and without recourse to liver biopsy. J Hepatol 2011; 54:586-7.
4. Castera L, Vergniol J, Foucher J, Le Bail B, Chanteloup E, Haaser M, et al. Prospective comparison of transient elastography, Fibrotest, APRI, and liver biopsy for the assessment of fibrosis in chronic hepatitis C. Gastroenterology. 2005; 128:343-50.
5. Sebastiani G, Halfon P, Castera L, Pol S, Thomas D L, Mangia A, et al. SAFE biopsy: a validated method for large-scale staging of liver fibrosis in chronic hepatitis. C. Hepatology. 2009 June; 49:1821-7.
6. Boursier J, Vergniol J, Sawadogo A, Dakka T, Michalak S, Gallois Y, et al. The combination of a blood test and Fibroscan improves the non-invasive diagnosis of liver fibrosis. Liver Int. 2009; 29:1507-15.
7. Boursier J, de Ledinghen V, Zarski J P, Rousselet M C, Sturm N, Foucher J, et al. A new combination of blood test and fibroscan for accurate non-invasive diagnosis of liver fibrosis stages in chronic hepatitis C. Am J. Gastroenterol. 2011; 106:1255-63.
8. Boursier J, de Ledinghen V, Zarski J P, Fouchard-Hubert I, Gallois Y, Oberti F, et al. Comparison of 8 diagnostic algorithms for liver fibrosis in hepatitis C: New algorithms are more precise and entirely non-invasive. Hepatology. 2011 September
9. Poynard T, Ingiliz P, Elkrief L, Munteanu M, Lebray P, Morra R, et al. Concordance in a world without a gold standard: a new non-invasive methodology for improving accuracy of fibrosis markers. PLoS One. 2008; 3:e3857.
10. Castéra L, Foucher J, Bernard P H, Carvalho F, Allaix D, Merrouche W, et al. Pitfalls of liver stiffness measurement: a 5-year prospective study of 13,369 examinations. Hepatology 2010; 51:828-35.
11. Poynard T, de Ledinghen V, Zarski J P, Stanciu C, Munteanu M, Vergniol J, et al. FibroTest and Fibroscan performances revisited in patients with chronic hepatitis C. Impact of the spectrum effect and the applicability rate. Clin Res Hepatol Gastroenterol. 2011 Aug. 16. [Epub ahead of print]
12. Rutjes A W, Reitsma J B, Coomarasamy A, Khan K S, Bossuyt P M. Evaluation of diagnostic tests when there is no gold standard. A review of methods. Health Technol Assess 2007; 11:1-51.
13. Poynard T, de Ledinghen V, Zarski J P, Stanciu C, Munteanu M, Vergniol J, et al. Relative performances of FibroTest, Fibroscan and biopsy for assessing the stage of liver fibrosis in patients with chronic hepatitis C: a step toward the truth in the absence of a gold standard. J Hepatol. 2011 Aug. 31.
14. Bedossa P, Dargère D, Paradis V. Sampling variability of liver fibrosis in chronic hepatitis C. Hepatology 2003; 38: 1449-57.
15. Rousselet M C, Michalak S, Dupre F, Croué A, Bedossa P, Saint-André J P, Calès P; Hepatitis Network 49. Sources of variability in histological scoring of chronic viral hepatitis. Hepatology. 2005; 41:257-64.
16. Mehta S H, Lau B, Afdhal N H, Thomas D L. Exceeding the limits of liver histology markers. J Hepatol 2009; 50:36-41.
17. Poynard T, Munteanu M, Deckmyn O, Ngo Y, Drane F, Messous D, et al. Applicability and precautions of use of liver injury biomarker FibroTest. A reappraisal at 7 years of age. BMC Gastroenterol 2011; 11:39
18. Friedrich-Rust M, Ong M F, Martens S, Sarrazin C, Bojunga J, et al. Performance of transient elastography for the staging of liver fibrosis: a metaanalysis. Gastroenterology 2008; 134: 960-974.
19. La Haute Autorité de Santé (HAS) in France—The HAS recommendations for the management of the chronic 20. Bedossa P, Poynard T. An algorithm for the grading of activity in chronic hepatitis C. The METAVIR Cooperative Study Group. Hepatology 1996; 24: 289-293.
21. Qu Y, Tan M, Kutner M H. Random effects models in latent class analysis for evaluating accuracy of diagnostic tests. Biometrics. 1996; 52:797-810.
22. Hadgu A, Qu Y. A biomedical application of latent class models with random effects. Applied Statistics 1998; 47, 603-616.
23. Vermunt J K, Magidson J. Technical Guide to Latent Gold 4.5. Belmont Mass.: Statistical Innovations 2007; Inc. LatentGold 4.5, Statistical Innovation, Belmont, Mass., USA.
24. Zhou X, Obuchowski N, McClish D. Statistical Methods in Diagnostic Medicine. John Wiley & Sons 2002.
25. Lambert J, Halfon P, Penaranda G, Bedossa P, Cacoub P, Carrat F. How to measure the diagnostic accuracy of noninvasive liver fibrosis indices: the area under the ROC curve revisited. Clin Chem. 2008; 54:1372-8.
26. Hintze J L. NCSS 2007 User Guide. Number Cruncher Statistical Systems software NCSS, Kaysville, Utah 2007.
27. Vergniol J, Foucher J, Terrebonne E, Bernard P H, Le Bail B, Merrouche W, et al. Non-invasive tests for fibrosis and liver stiffness predict 5-year outcomes of patients with chronic hepatitis C. Gastroenterology. 2011; 140: 1970-9.
28. Statistical Guidance on Reporting Results from Studies Evaluating Diagnostic Tests. http://www.fda.gov/MedicalDevices/DeviceRegulationandGuidance/GuidanceDocuments/ucm071148.htm
29. Lucidarme D, Foucher J, Le Bail B, Vergniol J, Castera L, Duburque C, et al. Factors of accuracy of transient elastography (FibroScan®) for the diagnosis of liver fibrosis in chronic hepatitis C. Hepatology 2009; 49:1083-9.
30. Myers R P, Crotty P, Pomier-Layrargues G, Ma M, Urbanski S J, Elkashab M. Prevalence, risk factors and causes of discordance in fibrosis staging by transient elastography and liver biopsy. Liver Int 2010; 30:1471-80.
31. Munteanu M, Ratziu V, Poynard T. The risk of multiplying diagnostic combinations in the absence of a perfect gold standard for a fibrosis test. Am J Gastroenterol 2011; 106:1853.
32. Poynard T, Ngo Y, Perazzo H, Munteanu M, Lebray P, Moussalli J, et al. Prognostic value of liver fibrosis biomarkers: a metaanalysis. Gastroenterol Hepatol 2011; 7:445-54.

The invention claimed is:

1. A method for treating liver cirrhosis in a patient suffering from liver fibrosis comprising the steps of:
   a) measuring values of alpha2-macroglobulin, haptoglobin, apolipoprotein-A1, total bilirubin, and gamma-glutamyl-transpeptidase (GGT) in serum or plasma of said patient, and combining said values through a first logistic function including said markers, age, and sex of said patient,
      wherein said first logistic function is 4.467×Log(Alpha2Macroglobulin (g/l))−1.357×Log(Haptoglobin (g/l))+1.017×Log(GGT (IU/l))+0.0281×Age (in years)+1.737 ×Log(Bilirubin (μmol/l))−1.184× ApoA1 (g/l)+0.301×Sex (female=0, male=1)−5.540, and obtaining a first index
   b) measuring liver stiffness for said patient by Vibration Controlled Transient Elastography and obtaining a second index,
   c) combining said first and second index through a second logistic function in order to obtain a final index,
      wherein said second logistic function is a1+a2×[first index] +a3×[second index] wherein
      a1 is comprised between −9.27 and −9.07;
      a2 is comprised between 3.08 and 3.1; and
      a3 is comprised between 5.67 and 5.87;
   d) diagnosing the level of liver cirrhosis in said patient based on the final index; and
   e) providing the patient with appropriate treatment depending on its level of liver cirrhosis.

2. A method for treating a patient suffering from advanced liver fibrosis comprising the steps of:
   a) measuring values of alpha2-macroglobulin, haptoglobin, apolipoprotein-A1, total bilirubin, and gamma-glutamyl-transpeptidase (GGT) in serum or plasma of said patient, and combining said values through a first logistic function including said markers, age, and sex of said patient, wherein said first logistic function is 4.467×Log(Alpha2Macroglobulin (g/l))−1.357×Log(Haptoglobin (g/l))+1.017×Log(GGT (IU/1))+0.0281× Age (in years)+1.737×Log(Bilirubin (μmol/l))−1.184× ApoA1 (g/l)+0.301×Sex (female=0, male=1)−5.540, and obtaining a first index
   b) measuring liver stiffness for said patient by Vibration Controlled Transient Elastography and obtaining a second index,
   c) combining said first and second index through a second logistic function in order to obtain a final index, wherein said second logistic function is b1+b2×[first index] +b3×[second index] wherein
      b1 is comprised between 2.35 and 2.55;
      b2 is comprised between 2.8 and 3; and
      b3 is comprised between 2.25 and 2.45;
   d) diagnosing the level of liver fibrosis in said patient based on the final index; and
   e) treating the patient according to the level of liver fibrosis.

3. The method of claim 1, wherein said second logistic function is −9.1753+3.0893×[first index] +5.7786×[second index].

4. The method of claim 2, wherein said second logistic function is 2.4518+2. 8935×[first index] +2.3657×[second index].

5. A method for treating liver fibrosis or cirrhosis in a patient comprising the steps of:
   a) measuring values of alpha2-macroglobulin, haptoglobin, apolipoprotein-A1, total bilirubin, and gamma-glutamyl-transpeptidase (GGT) in serum or plasma of said patient, and combining said values through a first logistic function including said markers, age, and sex of said patient,
      wherein said first logistic function is 4.467×Log (Alpha2Macroglobulin (g/l))−1.357×Log(Haptoglobin (g/l))+1.017×Log(GGT (IU/1))+0.0281×Age (in years)+1.737×Log(Bilirubin (μmol/l))−1.184× ApoA1 (g/l)+0.301×Sex (female=0, male=1)−5.540, and obtaining a first index
   b) measuring liver stiffness for said patient by Vibration Controlled Transient Elastography and obtaining a second index,
   c) combining said first and second index through a second logistic function in order to obtain a final index, wherein said second logistic function is a1+a2×[first index] +a3×[second index] wherein
a1 is comprised between −−9.27 and −9.07;
a2 is comprised between 3.08 and 3.1; and
a3 is comprised between 5.67 and 5.87,
d) diagnosing the level of liver cirrhosis in said patient based on the final index, and
e) classifying said patient as METAVIR F4 if the result of the second logistic function is higher or equal to 0.25, and
f) if the result of the second logistic function is lower than 0.25, classifying said patient with a METAVIR score using the result of the first logistic function, and
g) treating the patient according to the level of liver fibrosis or cirrhosis.

* * * * *